United States Patent [19]

Radebaugh et al.

[11] Patent Number: 5,200,193
[45] Date of Patent: Apr. 6, 1993

[54] PHARMACEUTICAL SUSTAINED RELEASE MATRIX AND PROCESS

[75] Inventors: Galen W. Radebaugh, Maple Glen; Thomas N. Julian, Horsham; Robert Glinecke, Glenside, all of Pa.

[73] Assignee: McNeilab, Inc., Spring House, Pa.

[21] Appl. No.: 600,279

[22] Filed: Oct. 22, 1990

Related U.S. Application Data

[63] Continuation of Ser. No. 184,532, Apr. 21, 1988, abandoned, which is a continuation-in-part of Ser. No. 41,164, Apr. 22, 1987, Pat. No. 4,245,286.

[51] Int. Cl.$^5$ .................................................. A61R 9/72
[52] U.S. Cl. .................................. 424/468; 424/472; 424/469; 424/470
[58] Field of Search ............... 424/468, 472, 469, 470

[56] References Cited

U.S. PATENT DOCUMENTS

| | | | |
|---|---|---|---|
| 3,121,044 | 2/1964 | Buckwalter et al. | 167/82 |
| 3,773,921 | 11/1973 | Sheth et al. | 424/19 |
| 3,965,256 | 6/1976 | Leslie | 424/22 |
| 4,083,949 | 4/1978 | Benedikt | 424/459 |
| 4,189,469 | 2/1980 | Gleixner et al. | 424/80 |
| 4,264,573 | 4/1981 | Powell et al. | 424/19 |
| 4,308,251 | 12/1981 | Dunn et al. | 424/19 |
| 4,439,453 | 3/1984 | Vogel | 424/324 |
| 4,465,660 | 8/1984 | David et al. | 424/15 |
| 4,601,894 | 7/1986 | Hanna et al. | 424/19 |
| 4,684,516 | 8/1987 | Bhutani | 424/19 |
| 4,702,918 | 10/1987 | Ushimaru et al. | 424/461 |
| 4,753,801 | 6/1988 | Oren et al. | 424/465 |
| 4,806,359 | 2/1989 | Radebaugh et al. | 424/470 |

FOREIGN PATENT DOCUMENTS 0159852 9/1985 United Kingdom .

OTHER PUBLICATIONS

"Hardness Increase etc" Chowan et al. Journ. of Pharmaceutical Science, vol. 67, No. 11, pp. 1385-1389, Oct., 1978.

*Primary Examiner*—Thurman K. Page
*Assistant Examiner*—Leon R. Horne

[57] ABSTRACT

A pharmaceutical sustained release homogeneous tablet or homogeneous tablet layer is formed by making a wet granulation using povidone (PVP) in alcohol as the granulating fluid which is mixed with a pharmaceutical active, ethylcellulose, a wicking agent, e.g. microcrystalline cellulose, an erosion promoter, e.g. pregelatinized starch, then drying and milling the granulation and blending with a dry powdered erosion promotor, wicking agent, lubricant, e.g. magnesium stearate and glidant, e.g. silicon dioxide, and compressing the resultant granulation, which upon administration results in a long-lasting slow and relatively regular incremental release of the pharmaceutical active, and multi-layered pharmaceutical active tablets comprising immediate release and/or sustained release layers.

17 Claims, 1 Drawing Sheet

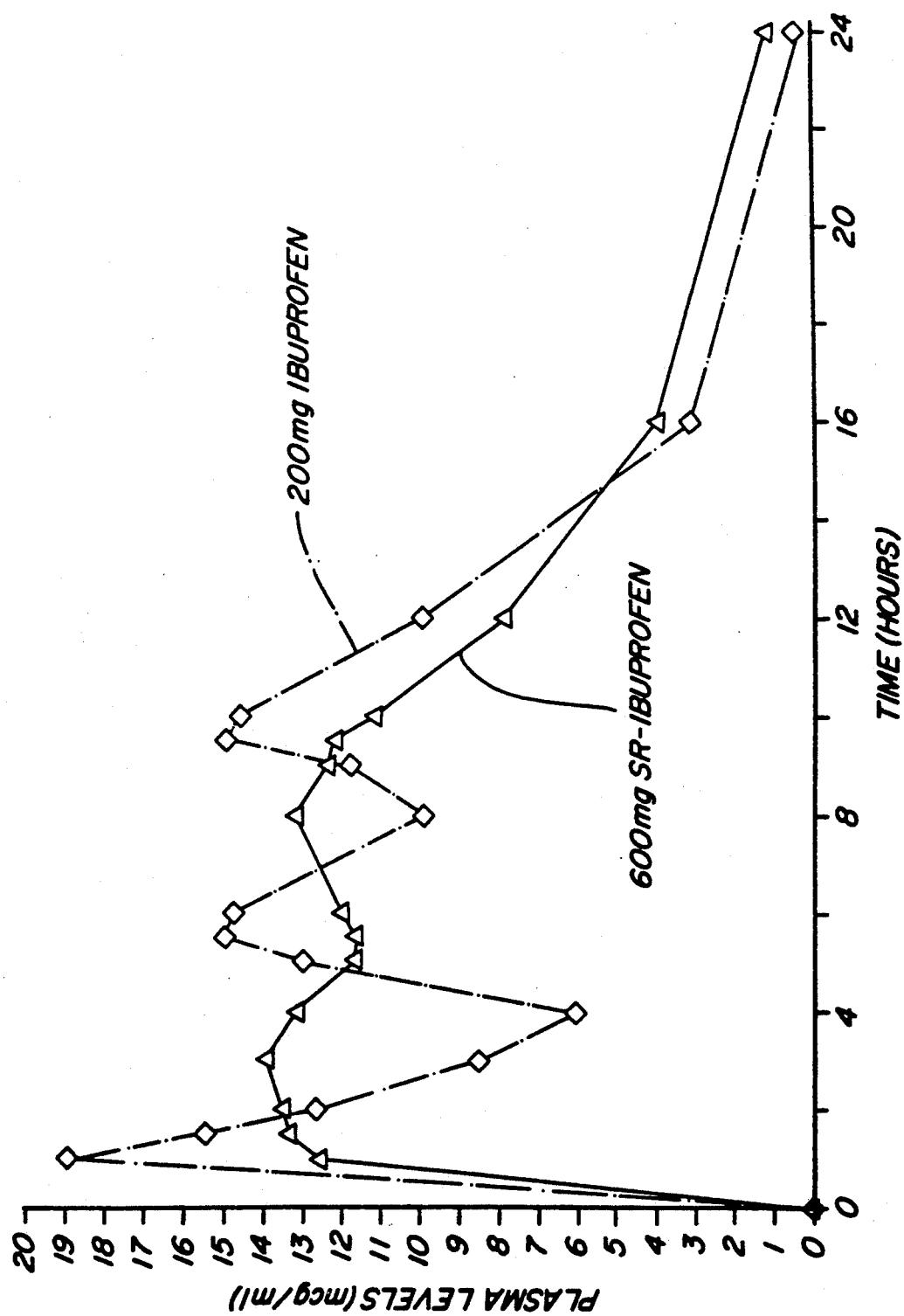

PHARMACEUTICAL SUSTAINED RELEASE MATRIX AND PROCESS

This is a continuation of application Ser. No. 184,532, filed Apr. 21, 1988 abandoned, which is a continuation-in-part application of U.S. Ser. No. 041,164 filed Apr. 22, 1987, which issued Feb. 21, 1989 as U.S. Pat. No. 4,245,286.

This invention relates to a sustained release form of orally administered pharmaceuticals, and is more particularly concerned with a pharmaceutical active disposed in a matrix formed from granulations of active mixed with inactive powdered excipients plus ethylcellulose using an aqueous-alcoholic solution of Povidone U.S.P. (polyvinylpyrrolidone—PVP) as the granulating fluid, which granulations are dried, milled, blended with additional inactive powdered excipients, and then compressed into a tablet, and to a process of making the pharmaceutical-containing matrix in a manner so that the rate of release of the active can be easily varied or controlled.

BACKGROUND OF THE PRESENT INVENTION

Therapeutic treatment with many orally administered pharmaceutical compounds and mixtures thereof require a patient to take successive dosages of the compounds every four hours. The requirement of such dosage regimens is a function of normal body metabolism of the active ingredients in pharmaceutical compounds. For example treatment with ibuprofen over a long period of time, e.g., over 12 hours, requires a patient to typically take one 200 mg. tablet or caplet, another four hours later, and a third four hours after that. In doing so, the levels of the ibuprofen in blood plasma will reach peak levels shortly after the ibuprofen tablets are taken, and then the plasma levels will decrease fairly rapidly. It is desirable to reduce the number of peaks and valleys to have a more uniform rate of release of orally administered pharmaceuticals into the blood plasma leading to more uniform or constant concentrations of pharmaceutical active in the plasma. Using the present invention, for example, a single 600 mg. active tablet or caplet can be formulated which has a sustained rate of release of active resulting in much more even plasma levels over twelve (12) hours, as contrasted to three (3) 200 mg. tablets or caplets. In addition, the quantity (amount) of the matrix can be adjusted up or down to produce tablets for sustained release that have more than or less than 600 mg. of pharmaceutical active. For example, a tablet with a sustained release analagous to the 600 mg. tablet but containing 800 mg. of pharmaceutical active can be manufactured from the same matrix composition by simply increasing the size and weight of the final tablet by a multiple of 4/3.

The present invention can be utilized to obtain sustained release pharmaceutical active tablets of many different time dosages, e.g., an 800 mg. sustained release tablet which results in desired blood plasma levels over twelve (12) hours, or a 400 mg. tablets with a similar blood plasma level over a shorter time period, e.g. six (6) hours. From a practical standpoint twelve (12) hours might be the most desired interval because of normal rates of metabolism and sleeping cycles of patients.

The matrix of the present invention can be utilized to make sustained release pharmaceutical preparations in compressed tablet form. The matrix materials used are compressed into a shaped tablet form. The term "tablet" as used herein includes tablets of any shape, and includes caplets, which are tablets having a capsule shape.

Some controlled release formulations for tablets are known. Dunn et al. U.S. Pat. No. 4,308,251 (see, Example 38) discloses ibuprofen controlled-release tablets containing in carefully controlled amounts, both an erosion-promoter agent, specifically, corn starch, and a release-controlling agent, specifically, cellulose acetate phthalate. The process disclosed is to intimately mix the ibuprofen with corn starch, and to add this mixture to a solution of ethanol and methylene chloride containing cellulose acetate phthalate to form granules, which are dried, blended with colloidal silicon dioxide, and compressed into tablets. The Dunn et al. patent suggests at column 5 that (1) while the preferred release controlling agent is cellulose acetate phthalate, various other suitable agents may be used, including ethyl cellulose, and (2) while the preferred erosion-promoting agent is corn starch, various other suitable agents may be used including various vegetable starches, cellulose derivatives and cross-linked polyvinylpyrrolidone. The instant invention utilizes similar alternative ingredients but in a different manner. In the instant invention the ethyl cellulose is mixed with ibuprofen as a dry powder while a non-crosslinked PVP, which is a completely different material with different properties than the cross-linked Dunn, et al. material, is dissolved in alcohol, which is also not taught by Dunn et al. Further, different proportions of ingredients are used to make a different type of controlled-release tablet than Dunn et al.

Bhutani U.S. Pat. No. 4,684,516 discloses sustained release pharmaceutical tablets prepared by compressing together an agglomeration of distinct sets of time release coated active particles. For example, active particles are broken up into three distinct sets and each set is coated with a prescribed amount of time release coating material to provide three separate release times for the active materials. The three sets of coated particles are then pressed together in a single pill to provide a timed interval release effect for the active material. The Bhutani "agglomeration" does not provide a gradual and consistent sustained release of active but rather a jagged release of active over a set amount of intervals. Further, the Bhutani type method of separately coating particles is cumbersome and expensive and provides pills of high bulk with unfavorably low drug/inactive-excipient ratios.

Ethylcellulose is often used as a coating for particles or in combination with another polymer. Ethylcellulose and PVP have even been used together in food supplements, e.g., German Offenlegusgsschrift DE 3331262A1, published Mar. 1, 1984, discloses amino acid food supplement coated with PVP and ethylcellulose. The PVP and ethylcellulose coating thereon acts as a barrier against release and digestion of the food supplement in certain parts of the gastrointestinal tract and assures release at a later time in a targeted area of the gastrointestinal tract. This product does not provide a gradual and consistent release of food materials but rather a delayed and contemporaneous release of food materials at a desired place in the body.

It is therefore an object of the present invention to provide a novel process and matrix for sustained gradual and consistent release of pharmaceutical actives in a low bulk homogeneous form.

SUMMARY OF THE INVENTION

The foregoing object of providing a novel process of making and a matrix for sustained release of pharmaceutical active compositions has now been accomplished by use of a homogeneous drug/binder matrix in accordance with the compositions and methods of the invention as described herein.

In accordance with the purposes of the invention, as embodied and fully described herein, the invention comprises a process of preparing a pharmaceutical active sustained release homogeneous tablet or tablet layer. The sustained release tablet or tablet layer is prepared by:

A) forming a granulating agent by dissolving 5–30 parts, by weight of the total non-active components (non-active components are those not pharmaceutically or therapeutically active) of the composition in dry powder form, of povidone in alcohol or an alcohol-water mixture;

B) blending together the following ingredients in dry powder form: an effective amount of pharmaceutical active which is sufficient to comprise about 66 to 96 percent by weight of the total composition in dry powder form; and the following amounts of non-active ingredients given in a range of parts by weight of the total non-active components of the tablet;

| Ingredient | Parts by Weight |
|---|---|
| ethylcellulose | 3–12 |
| wicking agent | 10–35 |
| erosion promoter | 5–25 |

C) adding the granulating agent from Step A to the blended powders from Step B, and forming a wet granulation thereof;

D) drying the wet granulation of Step C;

E) milling the dried granulation from Step D;

F) thoroughly blending the milled dried granulation from Step E with the following ingredients in dry powder form;

| Ingredient | Parts by Weight |
|---|---|
| erosion promoter | 1–20 |
| wicking agent | 3–20 |
| lubricant | 0–10 |
| glidant | 0–10 |

G) compressing the final granulation from Step F into a tablet or tablet layer wherein the active to non-active component ratio is at least 2:1.

As embodied and described herein the invention also comprises shaped and compressed sustained release therapeutic compositions comprising an effective amount of a therapeutically-active medicament and a granulating agent and excipients combined into a matrix, characterized by a long-lasting slow and relatively regular incremental release of the active medicament upon administration, wherein the granulating agent and excipients includes a combination of two polymers, ethylcellulose and povidone, and wherein the total amount of granulating agent and excipients is sufficient to effectively provide a solid sustained release matrix but generally, more than about 4 percent but less than one third (less than 33 percent), and preferably about 10 to 20 percent of the weight of said shaped and compressed composition.

In other preferred embodiments, the invention comprises a shaped and compressed bi-layer immediate release and sustained release therapeutic composition comprising a therapeutically-active medicament in both layers wherein the immediate release layer comprises the medicament and pharmaceutically acceptable excipients and the sustained release layer comprises a granulating agent and excipietns combined into a matrix, characterized by a long-lasting slow and relatively regular incremental release of medicament upon administration, wherein the granulating agent and excipients includes a combination of two polymers, ethylcellulose and povidone, and wherein the total amount of granulating agent and excipients is less than one third of the weight of the sustained release layer of said shaped and compressed bi-layer composition.

In further preferred embodiments, the invention comprises multilayered shaped and compressed compositions which include one or more layers of sustained release compositions in accordance with the invention. Also multilayer compositions comprising one or more immediate release and one or more sustained release composition layers are contemplated in accordance with the invention.

BRIEF DESCRIPTION OF THE DRAWING

The drawing is a graphic representation of the concentration of ibuprofen in the blood plasma of test subjects over a period of 12 hours.

DETAILED DESCRIPTION OF THE PREFERRED EMBODIMENTS OF THE INVENTION

The sustained release matrix pharmaceutical tablets of the present invention are made by adding granulating fluid to a dry powder blend of active drug and inactive excipients to form wet granulations, which are then dried and finely divided, e.g., by being milled into powder form and then blended with additional inactive powdered excipients and compressed into tablets. They can be easily manufactured using conventional tabletting equipment.

The tablets of the present invention have many advantageous features. They are bioerodible when swallowed, leaving no insoluble tablet shaped device to be excreted or removed from the body. The sustained release matrix uses ethyl cellulose (Ethylcellulose NF) and povidone (Povidone USP, e.g. Plasdone* K29/32) as matrix binding agents for obtaining the sustained release effect. This unique combination of two relatively inexpensive, pharmaceutically acceptable polymers, in the relative proportions and in the manner used here is a major novel feature of the present invention. In the most preferred embodiments of the invention, the amount of ethylcellulose used is on the general order of two percent or less of the amount of pharmaceutical active, while the amount of povidone is on the general order of four percent or less of the amount of pharmaceutical active used. This means that the sustained release matrix of the present invention is capable of producing dosage forms having very high drug/matrix binding agent ratios.

The process and compositions of the invention provide for sustained release tablets with a generally constant rate of erosion and release of active ingredient in a surprisingly low bulk form. The present invention provides sustained release tablets with high drug to binding matrix ratios which provides for potent tablets of a most manageable and swallowable size. It is therefore now possible to provide up to 800 mg of active ingredient in a single sustained release tablet that may be readily swallowed. Advantages to a single tablet, taken once a day, which provides a profile of active ingredient in the blood similar or superior to that provided by taking smaller doses of drugs 3 to 6 times a day are abundant. Economically, administering of tablets by health professionals to invalids, children or the like, may be cut down from 3 to 6 times a day to once a day. Further advantages exists in geriatric treatment where the taking of one tablet a day is easier to manage and remember than taking as many as 3 to 6 tablets several times a day. Further, human nature would appear to dictate a reluctance to take too many pills too many times a day and the sustained release pills of the present invention would contribute to alleviate the problems of patients not wishing to take too many pills and hence the correct amounts of daily medication.

The invention may also provide therapeutic benefits for administering pharmaceutical actives that are advantageously absorbed by the body in a slow (long dosage/time) but continuous fashion. Examples of pharmaceuticals which are best given at low dosage/time are those that could be toxic if plasma levels, exceed acceptable safe levels, e.g. aminophylline theophylline.

An advantage of the process of this invention is that the rate of matrix erosion when the tablet is swallowed can be modified so that the degree and/or length of the sustained release effect of the matrix can be easily modified by simply altering the levels of the other excipients, aside from the ethylcellulose and the povidone (PVP). Thus, the rate of release of pharmaceutical active from the tablet for absorption into the bloodstream can be modified to match the desired blood plasma concentration versus time profile by increasing the relative amounts of wicking agent and/or erosion promoter to increase the release over time or by decreasing the relative amounts of these ingredients to decrease the rate of release. Conversely, the rate of release of the active ingredients can be increased by decreasing the relative amounts of ethycellulose and/or PVP or the rate can be decreased by increasing the relative amounts of ethylcellulose and/or PVP in the binder matrix.

The sustained release matrix of the present invention is pH independent. Hydration of the matrix by fluids in the gastrointestinal tract bioerodes the matrix allowing the pharmaceutical active to be exposed through bio-erosion. The rate of erosion and hence the rate of dissolution controls the absorption of the pharmaceutical active and the resultant plasma concentration versus time profiles. Merely changing the amount of any of the ingredients which are used for the purpose of erosion promotion will result in a change of the rate of erosion of the final tablet.

The rate of matrix erosion and thus the effective release time of the pharmaceutical active in a patient's body can be manipulated over a wide range of times. The complete release time for active materials can be a half hour or less, up to 12 hours or more. The complete release time is contemplated to be adjustable in accordance with the desired chemotherapeutant dosage/time treatment that is prescribed. Generally, times greater than 12 hours are not preffered, since an undissolved portion of the matrix may be egested from the body by normal body metabolism functions over time perods in excess of 12 hours. The sustained release matrix of the present invention can be used alone as a tablet (or caplet, which is a tablet shaped like a capsule), or as part of a multi-layered tablet. Sometimes it is desirable to have a multi-layered tablet with an immediate or quick-release layer to begin raising the blood levels of pharmaceutical active relatively quickly until the sustained release portion of the tablet can begin to take over the effect. Thus, one can use the present invention to prepare tablets with two or more layers, each with a significantly different release rate of the same component or different components where a combination of drugs is desired.

Pharmaceutical actives usable in accordance with the invention include all those that are advantageously administered in a gradual and/or sustained release manner. Such chemotherapeutants include but are not limited to analgesics (e.g. ibuprofen, codeine), antidepressants (e.g. amitrityline), appetite suppressants (e.g. phenylpropanolamine), antiarthritics (e.g. naproxen, indomethacin), antihistamines (e.g. chlorpheniramine maleate), anti-inflamatory agents (e.g. tolmetin), antiulcers (e.g. cimetidine), antitussives (e.g. dextromethorpan), decongestants (e.g. pseudoephedrine), antiasthmatics (e.g. aminophylline), antianginal (e.g. isosorbide dinitrate), antibiotics (e.g. ampicillin), antipsychotics (e.g. thioridazine) and pharmaceutically acceptable salts thereof.

In addition to the ethylcellulose and PVP polymers discussed above which are matrix binding agents, the commonly used excipients which are granulated with the pharmaceutical active include a wicking agent (to wick fluids into the matrix) such as microcrystalline cellulose and an "erosion promoter" such as pregelatinized starch. The wicking agent and erosion promoter act in concert to facilitate erosion of the solid matrix and release of pharmaceutical active dispensed therein. Additional excipients which are added to the granulated and dried ingredients include a lubricant such as magnesium stearate and a glidant, such as colloidal silicon dioxide. The lubricant and glidant optionally may be omitted, but are currently preferred ingredients which are useful in the process of forming the shaped and compressed tablet compositions.

In currently preferred embodiments sustained release matrix tablets of the present invention contain approximately 1.4 percent ethylcellulose and approximately 2.8 percent PVP, with the balance consisting of various pharmaceutically acceptable, common excipients. The tablets of the present invention have a very high drug-to-excipients ratio on the order of at least 2:1 pharmaceutical active to excipients by weight and preferably at least 5:1 but up to more than 10:1 of pharmaceutical active to excipients by weight. The preferred ratio will change for different pharmaceutical actives which have different tabletting properties, or for very potent pharmaceutical actives which require only small dosage amounts such as, e.g. theophylline. These ratios may also be manipulated as described above for preparing compositions with particular dosage/time profiles. These ratios may also be manipulated as described above for preparing compositions with particular dosage/time profiles.

For each of the ingredients used in the sustained release matrix of the present invention, aside from the pharmaceutical active, the ethylcellulose and PVP, there exists less preferred alternative or equivalent materials which could be used in its place. The following Table I lists: each of the various preferred ingredients, the purpose of the ingredient, the preferred usable weight range of the preferred ingredient, other less preferred alternatives or equivalents which can be substituted for the preferred ingredient and the preferred usable weight range of such alternate ingredient for a sustained release layer containing 440 mg. of pharmaceutical active. For tablets (caplets) of a higher or lower level of pharmaceutical active desired weight ranges or the amounts of ingredients and their ranges would be proportionately increased or decreased.

The ingredients are listed in Table I under Part I Excipients, Part II Granulating Agent, and Part III Excipients, since they are used in this manner in the Preferred process by which the tablets of the present invention are made.

this point a small amount of dry powdered excipients such as pregelatinized starch, microcrystalline cellulose, magnesium stearate, and colloidal silicon dioxide are added and mixed with the milled granulations, after which they are compressed thereby forming the sustained release matrix.

If desired, a pharmaceutically acceptable coloring agent may be added to one or more of the layers of the tablet. One way of doing this is to add a dry powdered lake to Part III of the Sustained Release Tablet.

If desired, the compressed tablet may be coated with a pharmaceutically acceptable polymer, gelatin, or sugar coating. Caffeine or other compatible additives may also be included within the tablet matrix.

While various listed ingredients in the specification and claims have the suffix "U.S.P." (U.S. Pharmacopia)

TABLE 1

SUSTAINED RELEASE MATRIX COMPONENTS

| Preferred Ingredient | Purpose | Range of Parts by Wt. of Non-Active Ingredients | Alt./or Equiv. | Parts by Wt. Range |
|---|---|---|---|---|
| Part I - Excipients | | | | |
| Ethylcellulose NF (Ethocel *N-10) | Matrix Binding Agent | 3-12 | | |
| Microcrystalline Cellulose NF (Avicel*) pH 101, 102, 103, 105 | Wicking Agent | 10-35 | Powdered Cellulose (Solka Floc*) | 10-35 |
| Pregelatinized Starch NF | Erosion Promoter | 5-25 | Starch NF (corn, wheat or potato) or rice | 5-25 |
| Part II - Granulating Agent | | | | |
| Povidone USP Plasdone/K 29/32 | Matrix Binding Agent | 5-14 30 | | |
| Alcohol USP | Solvent | | Dehydrated Alcohol USP, Methyl Alcohol USP, | |
| Purified Water USP | Solvent | | Isopropyl | |
| [alcohol can be used either alone, or with water in a ratio of up to about 1 part alcohol to 2 parts water] | | | | |
| Part III - Excipient | | | | |
| Pregelatinized Starch | Erosion Promoter | 3-20 | Starch NF (corn, wheat or potato) or rice starch | 3-20 |
| | | | Sodium Starch Glycolate NF (Explotab*) | 1-15 |
| | | | Croscarmellose Sodium NF (Ac Di Sol*) | 1-15 |
| | | | Crospovidone NF (Povidone XL*) | 1-15 |
| Microcrystalline Cellulose | Wicking Agent | 3-20 | Powdered Cellulose (Solka Floc*) | 3-20 |
| Magnesium Stearate NF | Lubricant | 0-10 | Stearic Acid NF | 0-10 |
| Colloidal Silicon Dioxide NF (Cab-O-Sil*) | Glidant | 0-10 | Fumed Silicon Dioxide (Syloid*) | 0-10 |

The preferred Process which is utilized to form the most preferred sustained release matrix of the present invention is to mix together the dry powdered active drug, the dry powdered matrix binding polymer, ethyl cellulose, and the dry powdered excipients, microcrystalline cellulose and pregelatinized starch in a mixer/granulator. A granulating agent (fluid or solution) is formed by mixing alcohol (ethanol) and water to obtain a 1:1 mixture, into which povidone is dissolved to obtain a 12.25 percent (weight-by-weight) solution. The resultant granulating agent is sprayed onto the above admixed powders while they are being mixed in the mixer/granulator so as to form a wet granulation. The wet granulation thus obtained is dried and milled. At or "NF" (National Formulary), this is intended only to better identify the ingredient, or its purity, and not to limit the invention in any way to the use of ingredients so marked, since identical materials are available under other designations, e.g. in foreign countries.

The following examples are illustrative of the most preferred embodiments of the present invention. Any of the alternative or equivalent ingredients shown in Table I could be substituted if desired.

EXAMPLES

Example I—Ibuprofen Sustained Release Bi-Layer Tablet

This example illustrates a bi-layer tablet in which there is both an immediate release layer and a sustained release layer. The immediate release layer is analogous in composition and manufacturing procedure to currently available over-the-counter ibuprofen non-sustained release tablets, except the amount of ibuprofen in this layer of the example is 160 mg instead of 200 mg. It is the sustained release layer which utilizes the matrix of the present invention.

The bi-layer tablet uses the following ingredients:

| Ingredient | mg/Tablet |
|---|---|
| A. Immediate Release Layer | |
| *Part I Active and Excipients* | |
| Ibuprofen USP | 160.0 mg |
| Microcrystalline Cellulose NF (Avicel PH 101) | 32.0 mg |
| Starch NF | 32.0 mg |
| Pregelatinized Starch NF (Starch 1500) | 16.0 mg |
| Sodium Starch Glycolate NF | 6.4 mg |
| *Part II Granulating Agent* | |
| Hydroxypropyl methylcellulose 2910 USP (Methocel E-5) | 1.6 mg |
| Purified Water USP | q.s. |
| *Part III Excipients* | |
| Sodium Starch Glycolate NF (Explotab) | 1.6 mg |
| Coloidal Silicon Dioxide NF | 0.8 mg |
| Total | 250.4 mg |
| B. Sustained Release Layer | |
| *Part I Active & Excipients* | |
| Ibuprofen USP | 440.0 mg |
| Ethylcellulose NF (Ethocel N-10) | 7.3 mg |
| Microcrystalline Cellulose NF (Avicel PH 101) | 22.0 mg |
| Pregelatinized Starch NF (Starch 1500) | 14.0 mg |
| *Part II Granulating Agent* | |
| Povidone USP (Plasdone K 29/32) | 14.7 mg |
| Alcohol USP ⎫ 1:1 mixture Purified Water USP ⎭ | q.s. |
| *Part III Running Powder* | |
| Pregelatinized Starch NF (Starch 1500 LM) | 8.0 mg |
| Microcrystalline Cellulose NF (Avicel PH 101) | 7.3 mg |
| Magnesium Stearate NF | 5.0 mg |
| Colloidal Silicon Dioxide NF (Cab-O-Sil) | 5.0 mg |
| Total | 523.3 mg |
| Total Tablet Weight | 773.7 mg |

The above ingredients are utilized to make a bi-layer tablet according to the following working directions:

WORKING DIRECTIONS

A. Immediate Release Layer
1. Weigh the components of Part I and preblend them in a high shear mixer (Fielder: impeller speed of approximately 118 RPM for 3 minutes).
2. Prepare the granulating agent (Part II) by dissolving the Hydroxypropyl Methylcellulose 2910 USP into the Purified Water USP (a ratio of 3.2 grams of hydroxypropyl methylcellulose to 200 grams water).
3. Deliver the granulating agent to the powders of Part I, in the high shear mixer. Granulate the mixture for 20 minutes (Fielder: impeller speed of approximately 118 RPM).
4. Remove the completed wet granulation from the high shear mixer and load into the product bowl of a fluid bed apparatus (e.g. Aeromatic or Glatt). With an inlet air temperature of approximately 60° C., dry the granulation to a moisture level of 0.5 to 1.1% as determined by loss on drying (e.g. Computrac). The wet granulation can also be dried on trays in drying ovens.
5. Sieve the dried granulation (e.g. Glatt Quick Sieve: Stator No. 3, Screen No. 1.5mm, 1000 RPM). Other machines such as a Fitzpatrick Communition Mill can be used.
6. Blend the sieved and dried granulation with the powders of Part III using a suitable mixer such as a twin-shell, ribbon or planetary mixer.

B. Sustained Release Layer
1. Weigh the components of Part I and Preblend them in a high shear mixer (Fielder: impeller speed of approximately 250 RPM for 1 minute).
2. Prepare the granulating agent (Part II) by dissolving the Povidone USP in a 1:1 mixture of alcohol USP and purified water USP (a ratio of 12.25 grams of povidone to 100 grams of alcohol/water).
3. Spray the granulating agent at a rate of 600ml/min. onto Part I in the high shear mixer. Granulate the mixture for one minute after the addition of Part II (Fielder: impeller speed of approximately 250 RPM).
4. Remove the completed wet granulation from the high shear mixer and load it into the product bowl of a fluid bed apparatus (e.g. Aeromatic or Glatt). With an inlet air temperature of approximately 60° C., dry the granulation to a moisture level of 0.3 to 0.8% as determined by loss on drying (e.g. Computrac). The wet granulation can also be dried on trays in drying ovens.
5. Sieve the dried granulation (Fitzpatrick Communition Mill, Model D6: medium speed, knives forward, 0.093 screen). Other machines such as Glatt Quick Sieve can also be used.
6. Blend the sieved and dried granulation with the powders of Part III using a suitable mixer such as a twin-shell, ribbon or planetary mixer.

C. Compression of Tablets or Caplets
1. Load the granulation of the immediate release layer into one hopper and the granulation of the sustained release layer into the second hopper of a bilayer tableting machine (e.g. Stokes Versapress). Compress tablets using 0.749×0.281×0.060 extra deep concave capsule shaped tooling. (Tablet tooling of other shapes such as oval or round can also be used). The sustained release layer has a target weight of 523.3 mg. and the immediate release layer has a target weight of 250.4 mg. Ideal tablet hardness immediately after compression is 11 to 12 Kp.

The tablets of Example I were tested in twelve adult human male subjects and compared to non-sustained release (immediate release only) tablets in a cross-over design. A single tablet of Example I, which contained 600 mg. of ibuprofen, was dosed at time=0 hour. The non-sustained tablets, each containing 200 mg. ibuprofen, were dosed at time=0 hours, 4 hours and 8 hours. Subjects were fasted hours prior to administration of the first dose. Blood samples were taken from each subject, in each dosing regimen at 0, 1, 1.5, 2, 3, 4, 5, 5.5, 6, 8, 9, 9.5, 10, 12, 16 and 24 hours. Plasma was separated from the blood and the concentration of ibuprofen in each sample was determined. The results are shown numerically in Tables 2a, and 2b and graphically in the drawing. The results show that one bi-layer tablet of Example 1 reduces the number of peaks and valleys of the Plasma concentration versus time profile and provides equivalent area under the curve (AUC) when compared to three non-sustained release tablets, each containing 200 mg. ibuprofen.

TABLE 2

Sustained Release Ibuprofen 600 mg. (Example 1) Average Plasma Concentration Levels of Ibuprofen (mcg/ml) in twelve subjects. Average AUC equaled 174 mcg/hr.

| TIME (Hours) Post Dosing | | | | | | | | | | | | | | | |
|---|---|---|---|---|---|---|---|---|---|---|---|---|---|---|---|
| 0 | 1.0 | 1.5 | 2.0 | 3.0 | 4.0 | 5.0 | 5.5 | 6.0 | 8.0 | 9.0 | 9.5 | 10. | 12 | 16 | 24 |

Average (mcg/ml)

| 0 | 12.3 | 12.6 | 13.7 | 11.5 | 9.7 | 9.2 | 9.6 | 9.9 | 11.6 | 11.4 | 11.4 | 11.7 | 8.8 | 4.0 | 1.5 |
|---|---|---|---|---|---|---|---|---|---|---|---|---|---|---|---|

Non-sustained Release Ibuprofen 200 mg. Tablets; Average Plasma Concentration Level of Ibuprofen (mcg/ml) for dosing at 0, 4 and 8 hours in twelve subjects. Average AUC equaled 180 mcg/hr.

| TIME (Hours) Post Dosing | | | | | | | | | | | | | | | |
|---|---|---|---|---|---|---|---|---|---|---|---|---|---|---|---|
| 0 | 1.0 | 1.5 | 2.0 | 3.0 | 4.0 | 5.0 | 5.5 | 6.0 | 8.0 | 9.0 | 9.5 | 10. | 12 | 16 | 24 |

Average (mcg/ml)

| 0 | 19.1 | 15.4 | 12.5 | 8.5 | 6.0 | 13.0 | 14.9 | 14.7 | 9.9 | 11.8 | 14.9 | 14.6 | 9.9 | 3.1 | 0.3 |
|---|---|---|---|---|---|---|---|---|---|---|---|---|---|---|---|

Example II—Ibuprofen Sustained Release Bi-layer Tablet Containing a Total of 800 mg. Ibuprofen This example illustrates a bi-layer tablet which is analogous to the tablet described in Example I, except all amounts of ingredients per tablet and final weight of the tablet are 4/3 times the amounts and final weight of Example I. The working directions for the immediate release layer and the sustained release layer are analogous to the working directions described in Example I. Tablets can be compressed using capsule, oval, round or other appropriately shaped tooling. The sustained release layer has a target weight of 697.8 mg. and the immediate release layer has a target weight of 333.8 mg.

| Ingredient | mg/Tablet |
|---|---|
| A. Immediate Release Layer | |
| Part I Active and Excipients | |
| Ibuprofen USP | 213.3 |
| Microcrystalline Cellulose NF (Avicel PH 101) | 42.7 |
| Starch NF | 42.7 |
| Pregelatinized Starch NF (Starch 1500) | 21.3 |
| Sodium Starch Glycolate NF (Explotab) | 8.5 |
| Part II Granulating Agent | |
| Hydroxypropyl Methylcellulose 2910 USP | 2.1 |
| Purified Water USP | q.s. |
| Part III Excipients | |
| Sodium Starch Glycolate NF (Explotab) | 2.1 |
| Colloidal Silicon Dioxide NF | 1.1 |
| B. Sustained Release Layer | |
| Part I Active and Excipients | |
| Ibuprofen USP | 586.7 |
| Ethylcellulose NF (Ethocel N-10) | 9.7 |
| Microcrystalline Cellulose NF (Avicel PH 101) | 29.3 |
| Pregelatinized Starch NF (Starch 1500) | 18.7 |
| Part II Granulating Agent | |
| Povidone USP (Plasdone K 29/32) | 19.6 |
| Alcohol USP (ethanol) 1:1 mixture Purified Water USP | q.s. |
| Part III Excipients | |
| Pregelatinized Starch NF (Starch 1500) | 10.7 |
| Microcrystalline Cellulose NF (Avicel PH 101) | 9.7 |
| Magnesium Stearate NF | 6.7 |
| Colloidal Silicon Dioxide NF (Cab-O-Sil) | 6.7 |
| Total | 697.8 |
| Total Tablet Weight | 1031.6 |

Example III—Ibuprofen Sustained Release Tablet Containing 600 mg. of Ibuprofen in Matrix Form This example illustrates a mono-layer (all matrix) tablet in which there is only a sustained release layer. The working directions are analogous to the working directions for the sustained release layer described in Example I except that the amounts of all ingredients are proportionally increased such that the final tablet contains 600 mg. ibuprofen. Tablets can be compressed using capsule, oval, round or other appropriately shaped tooling. The final target weight of the compressed tablet is 713.6 mg.

| Ingredient | Mg/tablet |
|---|---|
| Part I Active and Excipients | |
| Ibuprofen USP | 600 |
| Ethylcellulose NF (Ethocel N-10)0 | 10 |
| Microcrystalline Cellulose NF (Avicel PH 101) | 30 |
| Pregelatinized Starch NF (Starch 1500) | 19.1 |
| Part II Granulating Agent | |
| Povidone USP (Plasdone K 29/32) | 20 |
| Ethanol USP Purified Water USP | q.s. |
| Part III Excipients | |
| Pregelatinized Starch NF (Starch 1500) | 10.9 |
| Microcrystalline Cellulose NF (Avicel PH 101) 1:1 mixture | 10 |
| Magnesium Stearate NF | 6.8 |
| Colloidal Silicon Dioxide NF (Cab-O-Sil) | 6.8 |

-continued

| Ingredient | Mg/tablet |
|---|---|
| Total Tablet Weight | 713.6 |

Examples V–XII

Examples V–XII are prepared accordingly to the working directions as described in Example I but utilizing the following combination of ingredients:

| Ingredient | Ex. V mg/tab | Ex. VI mg/tab | Ex. VII mg/tab | Ex. VIII mg/tab | Ex. IX mg/tab | Ex. X mg/tab | Ex. XI mg/tab | Ex. XII mg/tab |
|---|---|---|---|---|---|---|---|---|
| Part I | | | | | | | | |
| Ibuprofen | 600. | 600. | 600. | 600. | — | — | — | — |
| Pseudoephedrine HCl | 120. | 120. | 120. | — | — | — | — | — |
| Chlorpheniramine Maleate | — | 12. | 12. | — | — | — | — | — |
| Dextromethorphan HBr | — | — | 60. | — | — | — | — | — |
| Codeine Phosphate | — | — | — | 90. | — | — | — | — |
| Tolmetin Sodium | — | — | — | — | 800. | — | — | — |
| Thioridazine | — | — | — | — | — | 600. | — | — |
| Cimetidine | — | — | — | — | — | — | 800. | — |
| Naproxen | — | — | — | — | — | — | — | 800. |
| Ethylcellulose | 12. | 12. | 13. | 12. | 13. | 12. | 13. | 13. |
| Microcrystalline Cellulose | 36. | 36. | 40. | 40. | 40. | 36. | 40. | 40. |
| Pregelatinized Starch | 23. | 23. | 25. | 25. | 25. | 23. | 25. | 25. |
| Part II | | | | | | | | |
| Povidone | 24. | 24. | 27. | 27. | 27. | 24. | 27. | 27. |
| Alcohol/water mixture | q.s. | q.s. | q.s. | q.s. | q.s. | q.s. | q.s. | q.s. |
| Part III | | | | | | | | |
| Pregelatinized Starch | 13. | 13. | 15. | 15. | 15. | 13. | 15. | 15. |
| Microcrystalline Cellulose | 12. | 12. | 13. | 13. | 13. | 12. | 13. | 13. |
| Stearic Acid or Magnesium Stearate | 8. | 8. | 9. | 9. | 9. | 8. | 9. | 9. |
| Colloidal Silicon Dioxide | 8. | 8. | 9. | 9. | 9. | 8. | 9. | 9. |

Example IV—Ibuprofen Sustained Release Tablet Containing 800 mg of Ibuprofen in Matrix Form This example illustrates a mono-layer (all matrix) tablet in which there is only a sustained release layer. The working directions are analogous to the working directions for the sustained release layer described in Example I except that the amounts of all ingredients are proportionally increased such that the final tablet contains 800 mg. ibuprofen. Tablets can be compressed using capsule, oval, round or other appropriately shaped tooling. The total tablet weight of the compressed tablet is 951.5 mg.

| Ingredient | mg/tablet |
|---|---|
| Part I Active Excipients | |
| Ibuprofen USP | 800 |
| Ethylcellulose NF (Ethocel N-10) | 13.3 |
| Microcrystalline Cellulose NF (Avicel PH 101) | 40 |
| Pregelatinized Starch NF (Starch 1500) | 25.5 |
| Part II Granulating Agent | |
| Povidone USP (Plasdone K 29/32) | 26.7 |
| Alcohol USP / Purified Water USP } 1:1 mixture | q.s. |
| Part III Excipients | |
| Pregelatinized Starch NF (Starch 1500) | 14.5 |
| Microcrystalline Cellulose NF (Avicel PH 101) | 13.3 |
| Magnesium Stearate NF | 9.1 |
| Colloidal Silicon Dioxide NF (Cab-O-Sil) | 9.1 |
| Total Tablet Weight | 951.5 |

The scope of the present invention is not limited by the description, examples and suggested uses herein and modifications can be made without departing from the spirit of the invention. The matrix of the invention may be used with virtually any pharmaceutical active or combination thereof. Other additives may be included in the sustained release matrix composition of the invention such as for example, flavoring or other additives which may increase the aesthetic qualities of the tablets or impart other desirable properties thereto.

Application of the compositions and methods of the invention and the products made thereby can be to various fields as would be presently and prospectively known and recognized by those skilled in the art. Application of the products of the invention to medical uses can be accomplished by any suitable therapeutic method and technique such as those known to those skilled in the chemotherapeutant art. Thus, it is intended that the present invention cover the modifications and variations of this invention provided that they come within the scope of the appended claims and their equivalents.

What is claimed is:

1. A shaped and compressed sustained release therapeutic composition comprising an effective amount of an analgesic and a granulating agent and excipients combined into a matrix, characterized by a long-lasting slow and relatively regular incremental release of the analgesic upon administration, wherein the granulating agent and excipients includes a combination of two polymers, ethylcellulose and povidone, wherein the total amount of granulating agent and excipients is an amount effective to form a solid matrix of active and binder materials and is less than 20 percent of the weight of said shaped and compressed composition wherein the total amount of granulating agent, and granulating agent and excipients is in the range of 5 to less than 20 percent of the weight of pair shaped and compressed composition.

2. The composition of claim 1 wherein the total amount of granulating agent and excipients is in the range of 10 to 20 percent of the weight of said shaped and compressed composition.

3. A shaped and compressed pharmaceutical active sustained release tablet made by wet granulating an analgesic and the Excipients of Part I with the Granulating Agent of Part II to form a granulation, drying and milling the granulation to form a resultant granulation, and then blending with the Excipients of Part III and compressing into a tablet, wherein the analgesic is added in Part I and comprises at least 66% of the total weight of the tablet and the ingredients of parts I, II and II consists essentially of the following:

| Ingredient | Parts by Weight Range Total Inactive Ingredients |
|---|---|
| Part I Excipients | |
| Ethyl Cellulose | 3–12 |
| Microcrystalline Cellulose | 10–35 |
| Pregelatinized Starch | 5–25 |
| Part II Granulating Agent | |
| Povidone | 5–10 |
| Alcohol or Alcohol-Water | |
| Part III Excipients | |
| Pregelatinized Starch | 3–20 |
| Microcrystalline Cellulose | 2–10 |
| Magnesium Stearate | 2–10 |
| Colloidal Silicon Dioxide | 2–10 | wherein Alcohol is selected from the group consisting of alcohol USP, dehydrated alcohol USP, methyl alcohol USP and isopropyl alcohol USP.

4. A shaped and compressed bi-layer immediate release and sustained release therapeutic composition comprising a pharmaceutical active in both layers wherein the immediate release layer comprises a pharmaceutical active and pharmaceutically acceptable excipients and the sustained release layer comprises a granulating agent and excipients combined into a matrix, characterized by a long-lasting slow and relatively regular incremental release of the pharmaceutical active upon administration and at least one pharmaceutical active in the sustained release layer is an analgesic wherein the granulating agent and excipients includes a combination of two polymers, ethylcellulose and povidone, and wherein the total amount of granulating agent and excipients is less than 20 percent of the weight of the sustained release layer of said shaped and compressed bi-layer composition.

5. The therapeutic composition of claim 4 wherein the immediate release layer comprises a pharmaceutical active; microcrystalline cellulose; starch; sodium starch glycolate; and a granulating agent.

6. The bi-layered therapeutic composition of claim 5 wherein the pharmaceutical active in both layers is the same or different and is selected from the group consisting of analgesics, antiarthritics, antiasthmatics, antidepressants, appetite suppressants, antihistamines, antibiotics, antipsychotics, anti-ulcers, anti-inflammatories, antitussives, antiaginals, decongestants and combinations thereof.

7. A shaped and compressed bi-layer composition according to claim 4 wherein the pharmaceutical active in both layers is the same.

8. A shaped and compressed multilayered therapeutic composition comprising at least two layers of a sustained release composition according to claim 4 wherein the pharmaceutical actives of each layer are different.

9. A shaped and compressed bi-layered immediate release and sustained release pharmaceutical active tablet made by combining an immediate release layer comprising a pharmaceutical active and pharmaceutically acceptable excipients with a sustained release layer made by wet granulating an analgesic and Excipients ingradients of Part II, to form a granulation drying and milling the granulation to form a resultant granulation then blending the resultant granulation with the Excipients of Part III and compressing the two layers into a tablet, wherein the ingredients of Parts I, II and III consist essentially of the following:

| Ingredient | Range of Parts by Weight |
|---|---|
| Part I | |
| Pharmaceutical Active | 170–2000 |
| Ethyl Cellulose | 3–12 |
| Microcrystalline Cellulose | 10–35 |
| Pregelatinized Starch | 5–25 |
| Part II Granulating Agent | |
| Povidone | 5–30 |
| Alcohol or Alcohol-Water | q.t. |
| Part III Excipients | |
| Pregelatinized Starch | 3–20 |
| Microcrystalline Cellulose | 2–10 |
| Magnesium Stearate | 2–10 |
| Colloidal Silicon Dioxide | 2–10 | wherein Alcohol is selected from the group consisting of alcohol USP, dehydrated alcohol USP, methyl alcohol USP, and isopropyl alcohol USP.

10. A multilayered composition according to claim 8 comprising at least one additional of an immediate release composition comprising a pharmaceutical active wherein the pharmaceutical active is the same or different as the pharmaceutical active comprising the sustained release layers.

11. A bi-layered tablet according to claim 9 wherein at least one layer comprises caffeine.

12. The composition of claim 1 wherein the excipients comprise a wicking agent and an erosion promoter.

13. The composition of claim 12 wherein the wicking agent is microcrystalline cellulose and the erosion promoter is pregelatinized starch.

14. The composition of claim 1 wherein the granulating agent comprises a mixture of: alcohol selected from the group consisting of alcohol USP, dehydrated alcohol USP, methyl alcohol USP and isopropyl alcohol USP; and povidone.

15. The composition of claim 4 wherein the excipients comprise a wicking agent and an erosion promoter.

16. The composition of claim 15 wherein the wicking agent is microcrystalline cellulose and the erosion promoter is pregelatinized starch.

17. The composition of claim 4 wherein the granulating agent comprises a mixture of povidone and alcohol selected from the group consisting of alcohol USP, dehydrated alcohol USP, methyl alcohol USP and isopropyl alcohol USP.

* * * * *

UNITED STATES PATENT AND TRADEMARK OFFICE
CERTIFICATE OF CORRECTION

PATENT NO. : 5,200,193
DATED : Apr. 6, 1993
INVENTOR(S) : Radebaugh et al.

It is certified that error appears in the above-indentified patent and that said Letters Patent is hereby corrected as shown below:

COLUMN 16:

Claim 10, line 38, after "additional" insert -- layer --.

Signed and Sealed this

Fifth Day of April, 1994

BRUCE LEHMAN

Attest:

Attesting Officer

Commissioner of Patents and Trademarks